(12) United States Patent
Kopperschmidt

(10) Patent No.: US 9,132,224 B2
(45) Date of Patent: Sep. 15, 2015

(54) DEVICE AND METHOD FOR DETECTING THE DIRECTION OF THE FLOW OF LIQUID THROUGH A DIALYZER

(75) Inventor: Pascal Kopperschmidt, Dittelbrunn (DE)

(73) Assignee: Fresenius Medical Care Deutschland GmbH, Bad Homburg (DE)

(*) Notice: Subject to any disclaimer, the term of this patent is extended or adjusted under 35 U.S.C. 154(b) by 403 days.

(21) Appl. No.: 13/813,490

(22) PCT Filed: Jul. 29, 2011

(86) PCT No.: PCT/EP2011/003832
§ 371 (c)(1),
(2), (4) Date: Mar. 26, 2013

(87) PCT Pub. No.: WO2012/016671
PCT Pub. Date: Feb. 9, 2012

(65) Prior Publication Data
US 2013/0193039 A1 Aug. 1, 2013

(30) Foreign Application Priority Data

Jul. 31, 2010 (DE) .......................... 10 2010 032 980

(51) Int. Cl.
*A61M 1/16* (2006.01)
*A61M 1/36* (2006.01)
*G01P 13/02* (2006.01)

(52) U.S. Cl.
CPC ............... *A61M 1/3663* (2013.01); *A61M 1/16* (2013.01); *A61M 1/1617* (2014.02); *G01P 13/02* (2013.01); *A61M 1/367* (2013.01); *A61M 2205/3368* (2013.01); *A61M 2205/702* (2013.01)

(58) Field of Classification Search
CPC ... A61M 1/16; A61M 1/1617; A61M 1/3663; A61M 1/367; A61M 2205/3368; A61M 2205/702; G01P 13/02
See application file for complete search history.

(56) References Cited

U.S. PATENT DOCUMENTS

| 4,324,662 A | 4/1982 | Schnell |
| 5,399,157 A | 3/1995 | Goux et al. |

(Continued)

FOREIGN PATENT DOCUMENTS

| CA | 2 336 923 A1 | 1/2000 |
| EP | 0 366 950 A1 | 5/1990 |

(Continued)

OTHER PUBLICATIONS

International Search Report from PCT/EP2011/003832 mailed on Nov. 16, 2011.

(Continued)

*Primary Examiner* — John Kim
(74) *Attorney, Agent, or Firm* — Kenyon & Kenyon LLP

(57) ABSTRACT

The present invention relates to a device and a method for detecting the direction of the fluid flow through a dialyzer, as well as an extracorporeal blood treatment apparatus which comprises a device for detecting the direction of the fluid flow through the dialyzer. The devices and methods according to the present invention are based on the change in a physical and/or chemical property, for example the substance concentration or the temperature, of a fluid flowing into the one chamber of the dialyzer and the measurement of the change in the physical and/or chemical property of the fluid flowing out of the one chamber of the dialyzer.

22 Claims, 3 Drawing Sheets

(56) References Cited

U.S. PATENT DOCUMENTS 5,830,365 A * 11/1998 Schneditz .................. 210/739
7,077,819 B1    7/2006 Goldau et al.

FOREIGN PATENT DOCUMENTS

| | | |
|---|---|---|
| EP | 1 938 847 A2 | 7/2008 |
| GB | 2 276 566 A | 10/1994 |
| WO | 00/02604 A1 | 1/2000 |
| WO | 00/38761 A2 | 7/2000 |

OTHER PUBLICATIONS

International Preliminary Report on Patentability from PCT/EP2011/003832 mailed on Feb. 5, 2013.

* cited by examiner

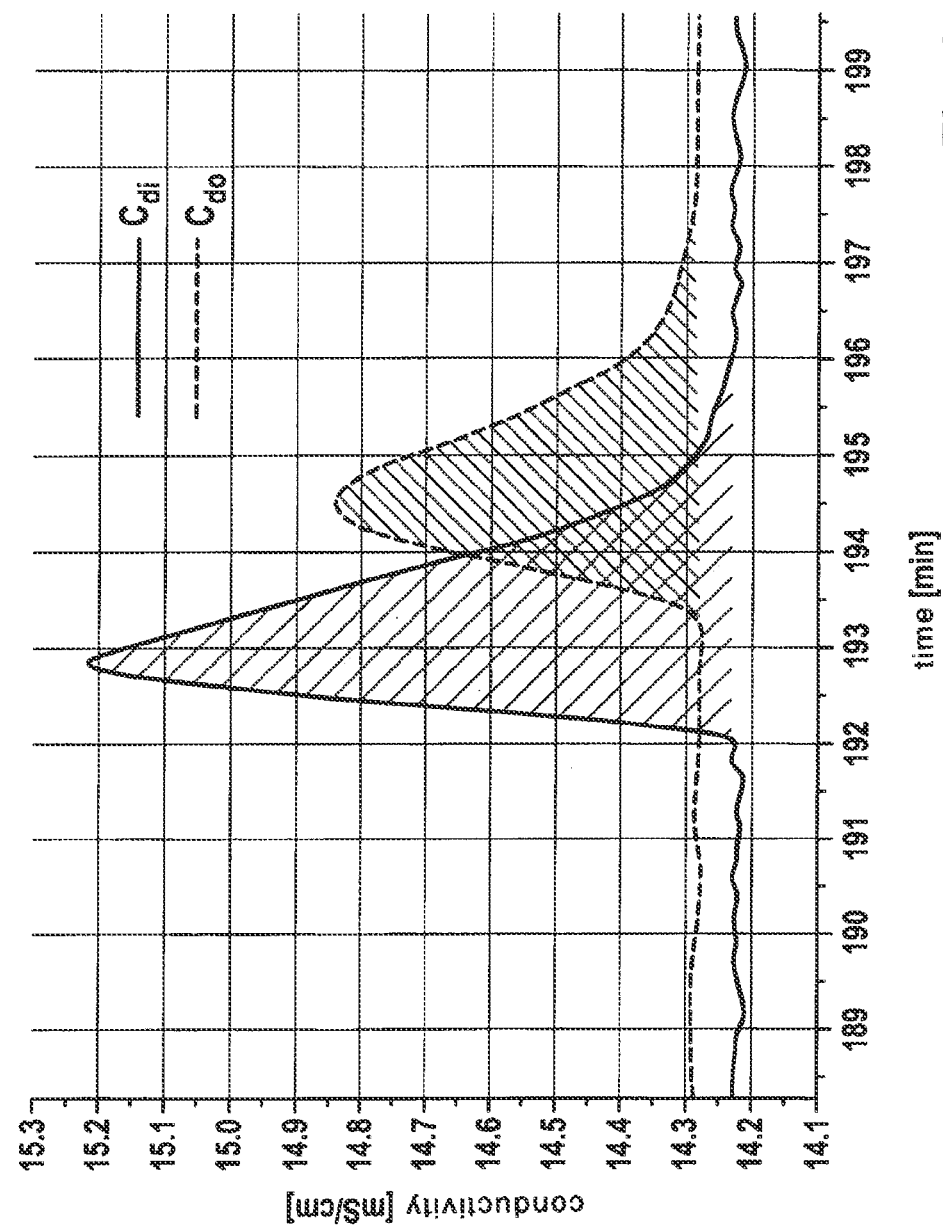

DEVICE AND METHOD FOR DETECTING THE DIRECTION OF THE FLOW OF LIQUID THROUGH A DIALYZER

CROSS REFERENCE TO RELATED APPLICATIONS

This is a 371 national phase application of PCT/EP2011/003832 filed Jul. 29, 2011, which claims priority from German Patent Application No. DE 10 2010 032 980.0, filed Jul. 31, 2010.

FIELD OF INVENTION

The present invention relates to a device and a method for detecting the direction of the fluid flow through a dialyzer, which comprises a first chamber which has a first and second connection and a second chamber which has a first and second connection, wherein the first chamber and the second chamber are separated from one another by a semipermeable membrane. Moreover, the present invention relates to an extracorporeal blood treatment apparatus with an extracorporeal blood circuit, which includes the blood chamber of a dialyzer divided by a semipermeable membrane into the blood chamber and a dialyzing fluid chamber, and with a fluid system which includes the dialyzing fluid chamber of the dialyzer, wherein the extracorporeal blood treatment apparatus comprises a device for detecting the direction of the fluid flow through the dialyzer.

BACKGROUND OF THE INVENTION

Various kinds of blood treatment apparatuses are known. The known blood treatment apparatuses include, for example, the apparatuses for hemodialysis, hemofiltration and hemodiafiltration. During the blood treatment, the patient's blood flows in an extracorporeal blood circuit through a blood treatment unit. In the case of the apparatuses for hemodialysis, hemofiltration and hemodiafiltration, the blood treatment unit is a dialyzer or filter, which is divided by a semi-permeable membrane into a blood chamber and a dialyzing fluid chamber. During the blood treatment, the blood flows through the blood chamber, while the dialyzing fluid flows through the dialyzing fluid chamber. An effective blood treatment requires that blood and dialyzing fluid flow in opposite directions along the membrane of the dialyzer or filter. In the case of an equi-directional flow, the blood treatment is less effective. In practice, therefore, the dialyzer or filter is operated not with an equi-directional flow, but with a counter-flow.

The dialyzer or filter is an interchangeable unit, which is connected to the fluid system of the blood treatment apparatus. The fluid system of the known blood treatment apparatuses comprises a line system with a first and a second line segment for the connection of the dialyzer. For the connection of the dialyzer to the fluid system, the first line segment is connected to the inlet of the dialyzing fluid chamber and the second line segment is connected to the outlet of the dialyzing fluid chamber of the dialyzer. The connection of the dialyzer takes place with known connection pieces, which include the known Hansen couplings.

The manufacturers of dialyzers and blood treatment apparatuses provide a color coding of the inlet and outlet of the dialyzer and of the Hansen couplings to be connected to the inlet and outlet, in order to make it easier for the user to make the connection according to the counter-flow principle. This color coding, however, is not uniform with all manufacturers. There is therefore the risk of the connections being confused. This will be referred to below as an incorrect connection.

If the dialyzer is not operated with a counter-flow, but with an equi-directional flow, the effectiveness of the treatment for the patient may be inadequate. This is particularly problematic when an incorrect connection of the dialyzer remains unnoticed. There is then the risk of the patient being treated with inadequate efficiency over a long period.

The problem underlying the present invention is to provide a device and a method for detecting the direction of the fluid flow through a dialyzer, in order to be able to check whether the dialyzer is being operated with an equi-directional flow or with a counter-flow. Moreover, the problem of the present invention is to provide an extracorporeal blood treatment apparatus with which the reliability in dialysis is increased.

The device according to the present invention and the method according to the present invention permit the monitoring of the connection of a dialyzer to the fluid system of an extracorporeal blood treatment apparatus. The detection of the direction of the fluid flow through the dialyzer of the extracorporeal blood treatment apparatus is based on the change in a physical and/or chemical property of a fluid flowing into the one chamber of the dialyzer and the measurement of the change in the physical and/or chemical property of the fluid flowing out of the one chamber of the dialyzer. The change in the physical and/or chemical property of the fluid downstream of the one chamber of the dialyzer traced back to the change in the physical and/or chemical property upstream of the one chamber of the dialyzer is measured before and after the reversal of the flow direction of the fluid through the one chamber of the dialyzer. A second fluid flows through the other chamber of the dialyzer, the flow direction whereof remains unchanged.

The flow reversal can take place in the whole fluid system or only in parts of the fluid system. For the flow reversal in the whole fluid system, the delivery direction of the delivery pump in the fluid system can be reversed. For the fluid reversal only in parts of the fluid system, a valve arrangement constituted in the manner of points can be used.

If the change in the physical and/or chemical property of the first fluid upstream of the one chamber of the dialyzer is known, the change in the physical and/or chemical property of the first fluid does not need to be measured. In the case where the physical and/or chemical property of the first fluid upstream of the one chamber of the dialyzer is however not known, the physical and/or chemical property of the first fluid is measured both upstream and downstream of the dialyzer.

The change in the physical and/or chemical property can take place through an increase and/or reduction of the physical and/or chemical property, whereby the change in the physical and/or chemical property can take place before and after the reversal of the flow direction by the same amount or different amounts. The physical and/or chemical property of the fluid is preferably changed by the same amount, which is preferably known. In this case, the change in the physical and/or chemical property only needs to be measured downstream of the one chamber of the dialyzer.

The first fluid flowing through the one chamber of the dialyzer can be dialyzing fluid, while the second fluid flowing through the second chamber of the dialyzer can be blood. In this case, the flow direction of the dialyzing fluid is reversed in the one chamber of the dialyzer. In principle, however, it is also possible to reverse the flow direction of the blood in the other chamber of the dialyzer.

If dialyzing fluid is flowing through the one chamber of the dialyzer and blood is flowing through the other chamber of the dialyzer, the detection of the flow direction through the dialyzer can take place during the blood treatment. It is however also possible to check the flow direction through the dialyzer before the blood treatment, if other fluids are flowing through the chambers of the dialyzer. Rinsing fluid can, for example, flow through one of the two chambers of the dialyzer.

For the detection of the flow direction through the dialyzer, it is basically irrelevant which physical and/or chemical property is changed. The concentration of a substance, for example the Na concentration, in one of the two fluids is preferably changed. It is however also possible to change the temperature of the fluid.

The change in the quantity of substance can easily take place in the dialysate preparation of the extracorporeal blood treatment apparatus. The temperature of the dialyzing fluid can also be changed in the dialysate preparation. The measurement of the concentration of a substance or the temperature of the fluid can take place with the known sensors, which are in any case generally present in the known blood treatment apparatuses. The method according to the present invention and the device according to the present invention can therefore easily be implemented in the known blood treatment apparatuses.

A preferred embodiment of the present invention makes provision to calculate the integral over the physical and/or chemical property of the fluid flowing into the first chamber of the dialyzer and the integral of the fluid flowing out of the first chamber of the dialyzer before and after the reversal of the flow direction, the operation of the dialyzer before the reversal of the flow direction with an equi-directional flow or with a counter-flow being determined on the basis of a comparison of the difference between the two integral values after the reversal of the flow direction with the difference between the two integral values before the reversal of the flow direction. The quotient of the difference between the two integral values after the reversal of the flow direction and the difference between the two integral values before the reversal of the flow direction is preferably calculated, it being concluded that there is an operation of the dialyzer before the reversal of the flow direction with an equi-directional flow if the quotient is greater than 1 or it being concluded that there is an operation of the dialyzer before the reversal of the flow direction with a counter-flow if the quotient is less than 1. In order to calculate the integral over the physical and/or chemical property, the area is calculated which is enclosed by the graph, which describes the physical and/or chemical property as a function of time, and the base line, which represents the constant quantity of the physical and/or chemical property. The points of intersection of this graph with the base line running parallel to the time axis define the integration limits. Only the pulse which is plotted on the base line is therefore integrated.

If a correct operation of the dialyzer is the operation with a counter-flow, an alarm, preferably an optical and/or acoustic and/or tactile alarm, is preferably emitted if it is established that, before the reversal of the flow direction, it can be concluded that there is an operation of the dialyzer with an equi-directional flow. In the case of an incorrect operation, a control signal for intervention into the machine control is preferably generated. The intervention into the machine control can consist in the fact that the performance of the blood treatment is prevented. This ensures that the blood treatment is only possible with a correct connection of the dialyzer. It is however also possible, as an intervention into the machine control, to reverse the flow direction so that the dialyzer is then operated correctly.

BRIEF DESCRIPTION OF THE DRAWINGS

An example of embodiment of the present invention is explained in greater detail below by reference to the drawings.

In the figures:

FIG. 2 shows the conductivity of the dialyzing fluid upstream and downstream of the one chamber of the dialyzer operated with a counter-flow as a function of time and FIG. 3 shows the conductivity of the dialyzing fluid upstream and downstream of the one chamber of the dialyzer operated with an equi-directional flow.

DETAILED DESCRIPTION

Figure 1:
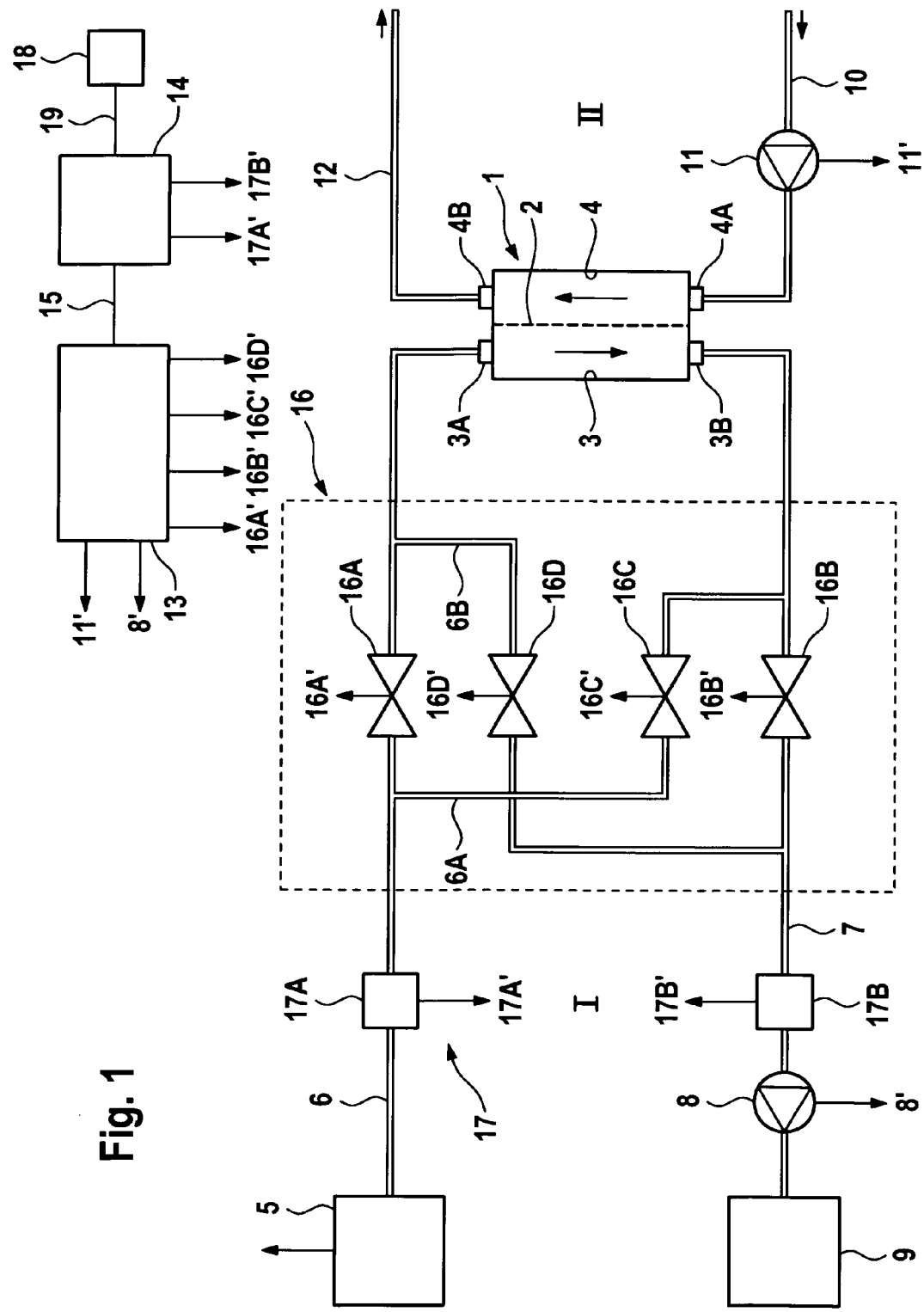
FIG. 1 shows, in a very simplified schematic representation, the main components of an extracorporeal blood treatment apparatus.

FIG. 1 shows, in a very simplified schematic representation, only the main components of a blood treatment apparatus essential to the present invention. In the present example of embodiment, the device for detecting the direction of the fluid flow through the dialyzer of the extracorporeal blood treatment apparatus is a component part of the blood treatment apparatus. The device for detecting the flow direction through the dialyzer can however also form a separate unit.

The extracorporeal blood treatment apparatus, which in the present example of embodiment is a hemodialysis apparatus, comprises a dialyzer 1 which is separated by a semi-permeable membrane 2 into a first chamber 3 and a second chamber 4. First chamber 3 comprises a first connection 3A and a second connection 3B, while the second chamber comprises a first connection 4A and a second connection 4B. In the present example of embodiment, the first chamber is dialyzing fluid chamber 3, while the second chamber is blood chamber 4.

The fluid system comprises a device 5, represented only schematically, with which fresh dialyzing fluid is prepared from water and concentrates. Device 5 for preparing the fresh dialyzing fluid permits a short-time change, in particular an increase in the concentrate composition, in order to produce a concentrate bolus. Moreover, device 5 permits the short-time change, in particular an increase in the temperature of the dialyzing fluid, in order to produce a temperature bolus.

Device 5 for the preparation of fresh dialyzing fluid is connected via a first dialyzing fluid line 6 to first connection 3A of dialyzing fluid chamber 3. A second dialyzing fluid line 7, into which a dialyzing fluid pump 8 is incorporated, leads from second connection 3B of dialyzing fluid chamber 3 to a drain 9. This part of the blood treatment apparatus represents dialyzing fluid system I.

An arterial blood line 10, into which a blood pump 11 is incorporated, leads from the patient to first connection 4A of blood chamber 4, while a venous blood line 12, which leads back to the patient, leads away from second connection 4B of blood chamber 4. This part of the blood treatment apparatus represents extracorporeal blood circuit II.

During the extracorporeal blood treatment, dialyzing fluid flows through dialyzing fluid chamber 3 and blood flows through blood chamber 4. The dialyzing fluid and the blood flow along membrane 2 of the dialyzer. In order to increase the efficiency of the treatment, dialyzer 1 is generally operated with a counter-flow. Here, dialyzing fluid and blood flow along the membrane in opposite directions. In principle, however, the dialyzer can also be operated with an equi-directional flow.

The blood treatment apparatus comprises a central control unit 13, which is connected via control lines 8', 11' to dialyzing fluid pump 8 and to blood pump 11.

First and second dialyzing fluid lines 6, 7 are hose lines, to which dialyzer 1 is connected. For the connection of hose lines 6, 7 to connections 3A, 3B of dialyzer 1, use is made of connection pieces (not shown), in particular Hansen couplings, which are generally color-coded.

The device for detecting the flow direction through dialyzer 1, which in the present example of embodiment is a component part of the blood treatment apparatus, comprises a computing and evaluation unit 14, which is connected via a data line 15 to central control unit 13 of the blood treatment apparatus. Computing and evaluation unit 14 can however also be a component part of control unit 13.

The detection of the flow direction through dialyzer 1 requires the reversal of the flow direction through the dialyzer. For this purpose, means 16 are provided for reversing the flow direction, said means comprising an arrangement of valves 16A, 16B, 16C, 16D. The valves are preferably electromagnetically or pneumatically operated valves, which are triggered via control lines 16A', 16B', 16C', 16D' by central control unit 13 of the blood treatment apparatus.

Valve 16A is disposed in first dialyzing fluid line 6 and second valve 16B in second dialyzing fluid line 7. Branching off from first dialyzing fluid line 6 upstream of first valve 16A is a first line branch 6A, which leads to second dialyzing fluid line 7 upstream of second valve 16B. Third valve 16C is incorporated into first line branch 6A. Downstream of first valve 16A, a second line branch 6B branches off from first dialyzing fluid line 6, which second line branch leads to second dialyzing fluid line 7 downstream of second valve 16B. Fourth valve 16D is incorporated into second line branch 6B. The terms upstream and downstream of the valves relate to the flow direction when the fluid flow is not reversed.

In the normal operation, dialyzer 1 is operated with a counter-flow. For this purpose, central control unit 13 opens first and second valves 16A, 16B and closes third and fourth valves 16C, 16D. Consequently, first connection 3A is the inlet and second connection 3B is the outlet of dialyzing fluid chamber 3. In order to reverse the flow direction, control unit 13 closes first and second valves 16A, 16B and opens third and fourth valves 16C, 16D. First connection 3A is then the outlet and second connection 3B is the inlet of dialyzing fluid chamber 3.

The device for detecting the flow direction through the dialyzer also comprises means for measuring a physical and/or chemical property of the dialyzing fluid. In the present example of embodiment, the physical and/or chemical property of the dialyzing fluid is either the concentration of a substance in the dialyzing fluid, for example the sodium concentration, or the temperature of the dialyzing fluid. In order to measure the physical and/or chemical property, means 17 are provided, which comprise a first sensor 17A and a second sensor 17B. In order to determine the Na concentration, first sensor 17A measures the conductivity of the dialyzing fluid in first dialyzing fluid line 6 upstream of dialyzer 1, while second sensor 17B measures the conductivity of the dialyzing fluid in second dialyzing fluid line 7 downstream of dialyzer 1 when the flow direction is not reversed. In an alternative embodiment, temperature sensors 17A, 17B are provided instead of conductivity sensors. Sensors 17A, 17B are connected via data lines 17A', 17B' to computing and evaluation unit 14.

Furthermore, an alarm unit 18 is provided, which is connected via a data line 19 to computing and evaluation unit 14.

Alarm unit 18 emits an optical and/or acoustic and/or tactile alarm when an incorrect operation of dialyzer 1 is ascertained.

The theoretical principles of the detection of the flow direction through the dialyzer will next be explained.

As a result of a short-time change in the concentration composition or the temperature of the dialyzing fluid in dialyzing fluid circuit I, a concentrate bolus or temperature bolus is produced, which is measured by sensors 17A and 17B.

The quantity of a substance of a specific concentration $c_{di}$, which is measured upstream of the dialyzer, is split up into a fraction $c_{bo}$, which passes over to the blood side, and a fraction $c_{do}$, which can be measured downstream of the dialyzer over a measurement time $\Delta t$:

$$Q_D \int_{\Delta t} c_{di}\, dt = Q_D \int_{\Delta t} c_{do}\, dt + Q_B \int_{\Delta t} c_{bo}\, dt \qquad [1]$$

The ratio of the integrals over the concentration downstream to upstream is a measure of dialysance $\Psi$ of the quantity of substance concerned.

$$\Rightarrow 1 - \frac{\int_{\Delta t} c_{do}\, dt}{\int_{\Delta t} c_{di}\, dt} = \frac{Q_B \int_{\Delta t} c_{bo}\, dt}{Q_D \int_{\Delta t} c_{di}\, dt} = \Psi \qquad [2]$$

The flow rate at which the quantity of substance on the dialysate side is transported is denoted by $Q_D$, and the flow rate at which the quantity on the blood side is moved is denoted by $Q_B$.

The obtained quantities of substance after reversal of the flow direction without a change in dialyzing fluid flow and blood flow $Q_D$, $Q_B$ are as follows:

$$Q_D \int_{\Delta t} \hat{c}_{di}\, dt = Q_D \int_{\Delta t} \hat{c}_{do}\, dt + Q_B \int_{\Delta t} \hat{c}_{bo}\, dt \qquad [3]$$

$$\Rightarrow 1 - \frac{\int_{\Delta t} \hat{c}_{do}\, dt}{\int_{\Delta t} \hat{c}_{di}\, dt} = \frac{Q_B \int_{\Delta t} \hat{c}_{bo}\, dt}{Q_D \int_{\Delta t} \hat{c}_{di}\, dt} = \hat{\Psi} \qquad [4]$$

The ratio of dialysance $\hat{\Psi}$ to $\Psi$ produces a number greater than or less than 1:

$$\frac{\hat{\Psi}}{\Psi} = \frac{\left(\int_{\Delta t} \hat{c}_{di}\, dt - \int_{\Delta t} \hat{c}_{do}\, dt\right) \int_{\Delta t} c_{di}\, dt}{\left(\int_{\Delta t} c_{di}\, dt - \int_{\Delta t} c_{do}\, dt\right) \int_{\Delta t} \hat{c}_{di}\, dt} \qquad [5]$$

The equations have to be adapted accordingly in the case of a change in blood flow or dialyzing fluid flow. Under identical boundary conditions, $C_{di} = \hat{c}_{di}$ can as a rule be adopted, because the pulse shape under identical boundary conditions, for example with the same dialysate flow and the same hose lengths, will look the same.

If the ratio $$\frac{\hat{\Psi}}{\Psi}$$

is less than 1, the flow between dialyzing fluid flow and blood flow during the measurement of $\hat{\Psi}$ is in the same direction and during the measurement of $\Psi$ is in opposite directions. The dialyzer is therefore being operated with a counter-flow.

If the ratio $$\frac{\hat{\Psi}}{\Psi}$$

is greater than 1, the flow between dialyzing fluid flow and blood flow during the measurement of $\hat{\Psi}$ is in opposite directions and during the measurement of $\Psi$ is in the same direction. The dialyzer is therefore being operated with an equi-directional flow.

The temperature measurement can take place in the same way as the conductivity measurement in order to analyse the flow through the dialyzer. For this purpose, the temperature is merely changed and measured instead of the conductivity.

The individual steps for performing the measurement are described in detail below.

It is assumed that the dialyzer is to be operated with a counter-flow. The counter-flow operation is therefore the normal operation. This is to be checked in the present example of embodiment. Valves 16A, 16B are opened and valves 16C, 16D are closed for the counter-flow operation.

The flow direction is first reversed in order to check the dialyzer connection. For this purpose, central control unit 13 closes valves 16A, 16B and opens valves 16C, 16D. A concentrate bolus is then produced. The concentrate bolus can be produced by changing the delivery quantity of the delivery pump (not represented) of device 5 for the preparation of the dialyzing fluid. Computing and evaluation unit 14 detects the conductivity with conductivity sensor 17A upstream of dialyzer 1 and conductivity sensor 17B downstream of the dialyzer. The conductivity can be measured continuously or discontinuously in a preset time interval in which the conductivity bolus is produced. The measured values are stored in a memory (not represented) of computing and evaluation unit 14.

Figure 2:
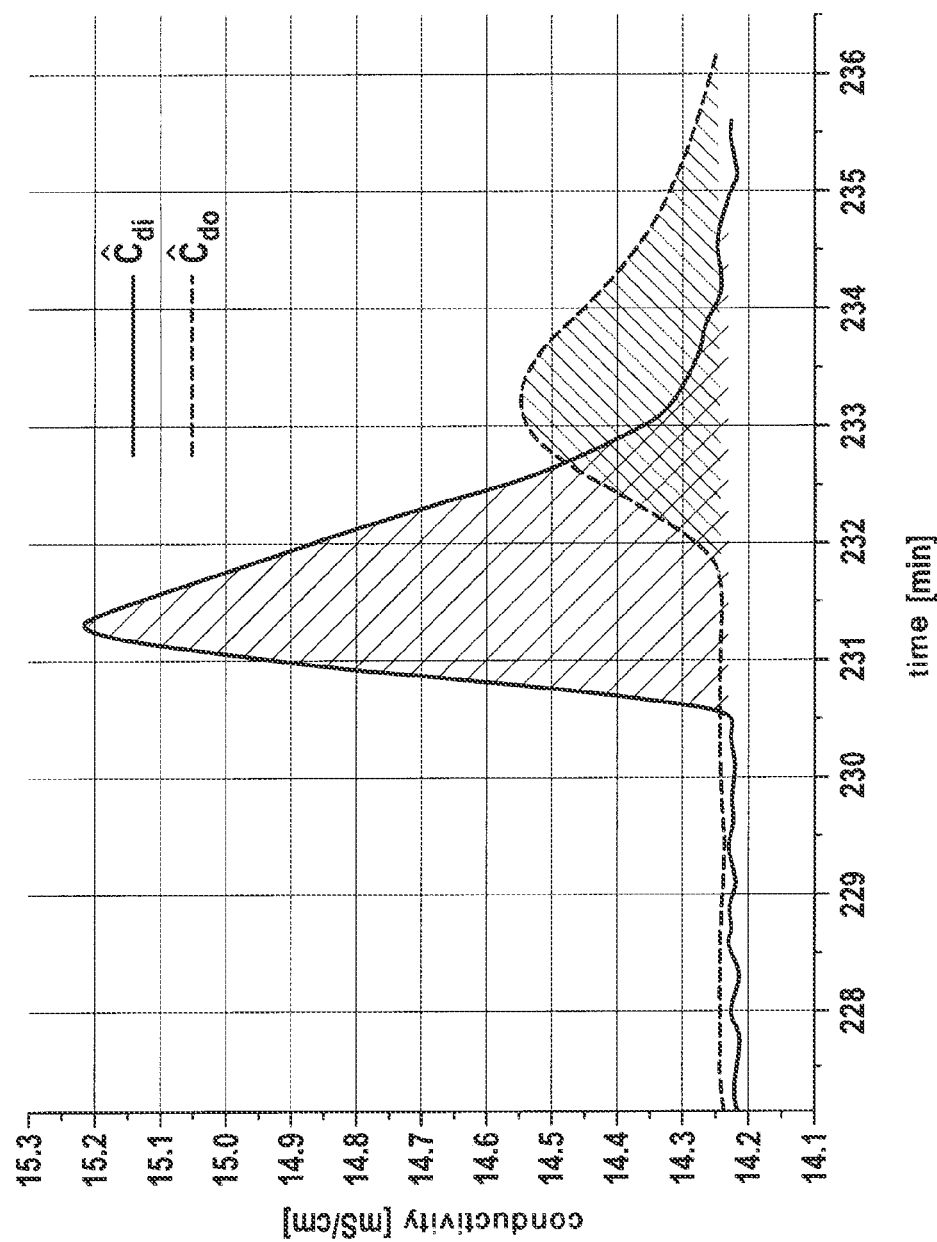

FIG. 2 shows the conductivity bolus, which is detected upstream and downstream of dialyzing fluid chamber 3 of dialyzer 1 with a reversed flow direction. In FIG. 2, the conductivity upstream is denoted by $\hat{c}_{di}$ and the conductivity downstream of the dialyzer is denoted by $\hat{c}_{do}$. It can be seen that conductivity bolus $\hat{c}_{di}$ upstream of the dialyzer is followed in time by conductivity bolus $\hat{c}_{do}$ downstream of the dialyzer.

The flow direction of the dialyzing fluid is then reversed again. For this purpose, valves 16C, 16D are closed and valves 16A, 16B are opened. A concentrate bolus is again produced after the reversal of the flow direction. The conductivity of the dialyzing fluid is measured upstream of the dialyzer with sensor 17A and downstream of the dialyzer with sensor 17B. The conductivity values are again stored in the memory of computing and evaluation unit 14.

FIG. 3 shows conductivity bolus $c_{di}$ upstream and conductivity bolus $c_{do}$ downstream of the dialyzer after the reversal of the flow direction, which corresponds to the normal operation of the dialyzer.

Computing and evaluation unit 14 now performs an integration over time of the conductivity measured with sensors 17A, 17B. Computing and evaluation unit 14 calculates the integral of the conductivity upstream of the dialyzer and the integral of the conductivity downstream of the dialyzer in a first measurement with a reversed flow direction and calculates the integral upstream of the dialyzer and the integral downstream of the dialyzer in the second measurement with the dialyzer in the normal operation. The integral over time is represented in the figures by a shaded area, which is bounded by the respective curve and the respective base line. Quotient $$\frac{\hat{\Psi}}{\Psi}$$

is calculated according to equation (5) with the calculated integral values upstream and downstream of the dialyzer after the reversal of the flow direction (first measurement) and before the reversal of the flow direction (second measurement). Computing and evaluation unit 14 compares quotient $$\frac{\hat{\Psi}}{\Psi}$$

with the value 1. If quotient $$\frac{\hat{\Psi}}{\Psi}$$

is less than 1, computing and evaluation unit 14 ascertains that the dialyzer has been operated with a counter-flow. In the case where the ratio is greater than 1, computing and evaluation unit 14 ascertains that the dialyzer has been operated with an equi-directional flow.

In the present case of a correct connection of the dialyzer, quotient $$\frac{\hat{\Psi}}{\Psi}$$

is less than 1. If the dialyzer is not correctly connected to dialyzing fluid lines 6, 7, i.e. the connections have been confused, the computing and evaluation unit ascertains that the dialyzer has been operated with an equi-directional flow. Computing and evaluation unit 14 then generates a control signal which is received by alarm unit 18. Alarm unit 18 now emits an alarm. Furthermore, computing and evaluation unit 14 generates a control signal which is received by central control unit 13. Control unit 13 then performs an intervention into the machine control. This intervention can consist in the fact that the performance of the blood treatment is interrupted. Alternatively, it is possible to reverse the flow direction by actuating corresponding valves 16A-16D, so that the dialyzer is operated with a counter-flow.

The following numerical values are adopted for the present example of embodiment:

If we let $C_{di} = \hat{c}_{di}$, $$\int_{\Delta t} c_{di}\, dt = 100, \int_{\Delta t} c_{do}\, dt = 40 \text{ and } \int_{\Delta t} \hat{c}_{do}\, dt = 70$$

follows according to equation [5]:

$$\frac{\hat{\Psi}}{\Psi} = \frac{(100-70)}{(100-40)} = \frac{30}{60} = 0.5 < 1 \qquad 5$$

In the second example of embodiment, the temperature is changed instead of the substance concentration. The calculation and the comparison of the integral values takes place in a similar manner to the first example of embodiment.

What is claimed is:

1. A device for detecting the direction of the fluid flow through a dialyzer which comprises a first chamber which has a first and second connection and a second chamber which has a first and second connection, wherein the first chamber and the second chamber are separated from one another by a semipermeable membrane, the device comprising:
a system for reversing the flow direction configured such that the dialyzer can be switched over between an equi-directional flow operation, wherein a first fluid flows into the first connection of the first chamber and the first fluid flows out of the second connection of the first chamber, while the second fluid flows into the first connection of the second chamber and the second fluid flows out of the second connection of the second chamber, and a counter-flow operation, wherein the first fluid flows into the second connection of the first chamber and the first fluid flows out of the first connection of the first chamber, while the second fluid flows into the first connection of the second chamber and the second fluid flows out of the second connection of the second chamber, or alternatively, between the counter-flow operation and the equi-directional flow operation;
a system for changing a physical and/or chemical property of the fluid flowing into the first and/or second connection of the first chamber,
a system for measuring the physical and/or chemical property of the fluid flowing out of the second and/or first connection of the first chamber, and
a computing and evaluation system cooperating with the system for measuring the physical and/or chemical property, said computing and evaluation system being configured such that, on the basis of the change in the physical and/or chemical property of the first fluid flowing out of the second and/or first connection of the first chamber, said change being measured before the reversal of the flow direction and after the reversal of the flow direction and being able to be traced back to the change in the physical and/or chemical property of the first fluid flowing into the first and/or second connection of the first chamber, it is concluded whether the dialyzer has been operated with an equi-directional flow operation or a counter-flow operation before the reversal of the flow direction.

2. The device according to claim 1, wherein the system for measuring the physical and/or chemical property is provided for measuring the physical and/or chemical property of the fluid flowing into the first and/or second connection of the first chamber.

3. The device according to claim 2, wherein the computing and evaluation system is configured such that an integral over the physical and/or chemical property of the first fluid flowing into the first connection of the first chamber and an integral of the first fluid flowing out of the second connection of the first chamber are calculated before the reversal of the flow direction and an integral over the physical and/or chemical property of the first fluid flowing into the second connection of the first chamber and an integral of the first fluid flowing out of the first connection of the first chamber are calculated after the reversal of the flow direction,
wherein the operation of the dialyzer before the reversal of the flow direction with an equi-directional flow or with a counter-flow is determined on the basis of a comparison of the difference between the two integral values after the reversal of the flow direction with the difference between the two integral values before the reversal of the flow direction.

4. The device according to claim 3, wherein the computing and evaluation system is configured such that a quotient of the difference between the two integral values after the reversal of the flow direction and a difference between the two integral values before the reversal of the flow direction is calculated,
wherein it is concluded that an operation of the dialyzer before the reversal of the flow direction is with an equi-directional flow if the quotient is greater than 1 or it is concluded that there is an operation of the dialyzer before the reversal of the flow direction with a counter-flow if the quotient is less than 1.

5. The device according to claim 1, wherein, the first fluid is dialyzing fluid.

6. The device according to claim 1, wherein the second fluid is blood.

7. The device according to claim 1, wherein the physical and/or chemical property is a concentration of a substance in the fluid, the system for measuring the physical and/or chemical property being a system for measuring the substance concentration.

8. The device according to claim 1, wherein the physical and/or chemical property is the temperature of the fluid, the system for measuring the physical and/or chemical property being a system for measuring the temperature.

9. The device according to claim 1, wherein the computing and evaluation system cooperates with an alarm system which emits an optical and/or acoustic and/or tactile alarm when the computing and evaluation system has ascertained an operation of the dialyzer with an equi-directional flow before the reversal of the flow direction.

10. The device according to claim 1, wherein the computing and evaluation system generates a control signal for an intervention into a machine control when the computing and evaluation system has ascertained an operation of the dialyzer with an equi-directional flow before the reversal of the flow direction.

11. The device according to claim 10, wherein the control signal for the intervention into the machine control is a control signal activating the system for reversing the flow direction.

12. An extracorporeal blood treatment apparatus comprising:
an extracorporeal blood circuit comprising a blood chamber of a dialyzer divided by a semi-permeable membrane into a blood chamber and a dialyzing fluid chamber, and a dialyzing fluid system which includes the dialyzing fluid chamber,
wherein the extracorporeal blood treatment apparatus comprises a device for detecting a direction of the fluid flow through a dialyzer according to claim 1.

13. A method for detecting the direction of the fluid flow through a dialyzer which comprises a first chamber which has a first and second connection and a second chamber which has a first and second connection, wherein the first chamber and the second chamber are separated from one another by a semipermeable membrane, the method comprising the steps of:

changing a physical and/or chemical property of a first fluid flowing into the first connection of the first chamber, while a second fluid flows into the first connection of the second chamber of the dialyzer and out of the second connection of the second chamber of the dialyzer, measuring the physical and/or chemical property of the first fluid flowing out of the second connection of the first chamber, which physical and/or chemical property can be traced back to the change in the physical and/or chemical property of the first fluid flowing into the first connection of the first chamber, reversing the flow direction such that the first fluid flows into the second connection of the first chamber and the first fluid flows out of the first connection of the first chamber, and, concluding whether the dialyzer has been operated in an equi-directional flow operation or in a counter-flow operation before reversal of the flow direction, wherein said concluding is made on the basis of the change in the physical and/or chemical property of the first fluid flowing out of the second and/or first connection of the first chamber, said change being measured before the reversal of the flow direction and after the reversal of the flow direction and being able to be traced back to the change in the physical and/or chemical property of the first fluid flowing into the first and/or second connection of the first chamber.

14. The method according to claim 13, wherein the physical and/or chemical property of the fluid flowing into the first and/or second connection of the first chamber is measured.

15. The method according to claim 14, wherein an integral over the physical and/or chemical property of the first fluid flowing into the first connection of the first chamber and an integral of the first fluid flowing out of the second connection of the first chamber are calculated before the reversal of the flow direction, and an integral over the physical and/or chemical property of the first fluid flowing into the second connection of the first chamber and an integral of the first fluid flowing out of the first connection of the first chamber are calculated after the reversal of the flow direction, wherein the operation of the dialyzer before the reversal of the flow direction with an equi-directional flow or with a counter-flow is determined on the basis of a comparison of a difference between the two integral values after the reversal of the flow direction with a difference between the two integral values before the reversal of the flow direction.

16. The method according to claim 15, wherein a quotient of the difference between the two integral values after the reversal of the flow direction and a difference between the two integral values before the reversal of the flow direction is calculated, wherein it is concluded that there is an operation of the dialyzer with an equi-directional flow before the reversal of the flow direction if the quotient is greater than 1 or it is concluded that there is an operation of the dialyzer with a counter-flow before the reversal of the flow direction if the quotient is less than 1.

17. The method according to claim 13, wherein the first fluid is dialyzing fluid.

18. The method according to claim 13, wherein the second fluid is blood.

19. The method according to claim 13, wherein the physical and/or chemical property is the concentration of a substance in the fluid.

20. The method according to claim 13, wherein the physical and/or chemical property is the temperature of the fluid.

21. The method according to claim 13, wherein an optical and/or acoustic and/or tactile alarm is emitted if, before the reversal of the flow direction, an operation of the dialyzer with an equi-directional flow is ascertained.

22. The method according to claim 13, wherein a control signal for an intervention into a machine control is generated if, before the reversal of the flow direction, an operation of the dialyzer with an equi-directional flow is ascertained.

\* \* \* \* \*